(12) United States Patent
Eimann et al.

(10) Patent No.: US 10,478,347 B2
(45) Date of Patent: Nov. 19, 2019

(54) NOZZLE ASSEMBLY USED TO MANUFACTURE ABSORBENT ARTICLES

(71) Applicant: The Procter & Gamble Company, Cincinnati, OH (US)

(72) Inventors: Klaus Eimann, Zellingen (DE); Uwe Schneider, Cincinnati, OH (US); Dirk Esser, Sierscheid (DE); Ricky Reynaldo Yanez, Jr., Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 252 days.

(21) Appl. No.: 15/628,678

(22) Filed: Jun. 21, 2017

(65) Prior Publication Data

US 2018/0369024 A1 Dec. 27, 2018

(51) Int. Cl.
*B29C 65/00* (2006.01)
*B29C 65/52* (2006.01)
(Continued)

(52) U.S. Cl.
CPC .. *A61F 13/15764* (2013.01); *A61F 13/15593* (2013.01); *A61F 13/15723* (2013.01);
(Continued)

(58) Field of Classification Search
CPC ......... B29C 65/00; B29C 65/02; B29C 65/14; B29C 65/16; B29C 65/48; B29C 65/52; B29C 65/524; B29C 65/525; B29C 65/56; B29C 65/562; B29C 65/564; B29C 65/72; B29C 66/00; B29C 66/301; B29C 66/71; B29C 66/712; B05C 5/0254;
(Continued)

(56) References Cited

U.S. PATENT DOCUMENTS

| 4,324,246 A | 4/1982 | Mullane et al. |
| 4,342,314 A | 8/1982 | Radel et al. |

(Continued)

FOREIGN PATENT DOCUMENTS

| EP | 1 635 750 B1 | 10/2009 | |
| WO | WO-2007049349 A1 * | 5/2007 | ........... B05C 5/0254 |

OTHER PUBLICATIONS

U.S. Appl. No. 15/599,500, filed May 19, 2017, Schneider.

*Primary Examiner* — Philip C Tucker
*Assistant Examiner* — Brian R Slawski
(74) *Attorney, Agent, or Firm* — Andrew J. Hagerty; Sarah M. DeCristofaro (57) ABSTRACT

A nozzle assembly may be used to apply fluid to an advancing substrate. The nozzle assembly includes a nozzle body made from a first material. The nozzle body may include one or more abrasion resistant materials fused to the nozzle body. The nozzle body may be configured to deposit a fluid, using a shim plate, onto the advancing substrate. As the substrate advances past the nozzle assembly, the substrate and/or the fluid may contact the nozzle assembly resulting in wear. The one or more abrasion resistant materials, which is different than the first material of the nozzle body, may be fused to a portion of the nozzle body to reduce the wear and prolong the life of the nozzle body. Thus, the portion of the nozzle body having the abrasion resistant material is restored rather than having to replace the entire nozzle body.

6 Claims, 8 Drawing Sheets

(51) Int. Cl.
*B29C 65/72* (2006.01)
*B29C 48/30* (2019.01)
*B29C 48/345* (2019.01)
*B32B 37/00* (2006.01)
*B05C 5/02* (2006.01)
*B05D 1/26* (2006.01)
*A61F 13/15* (2006.01)
*B23K 26/359* (2014.01)
*B05C 11/10* (2006.01)
*B29C 65/76* (2006.01)

(52) U.S. Cl.
CPC ...... *A61F 13/15756* (2013.01); *B05C 5/0254* (2013.01); *B05C 5/0258* (2013.01); *A61F 13/15739* (2013.01); *B05C 5/027* (2013.01); *B05C 5/0241* (2013.01); *B05C 11/1026* (2013.01); *B05D 1/265* (2013.01); *B23K 26/359* (2015.10); *B29C 48/3003* (2019.02); *B29C 48/345* (2019.02); *B29C 65/525* (2013.01); *B29C 65/72* (2013.01); *B29C 65/76* (2013.01); *B29C 66/301* (2013.01); *B29C 66/712* (2013.01)

(58) Field of Classification Search
CPC ... B05C 5/0258; B05C 11/10; B05C 11/1002; A61F 13/15577; A61F 13/15585; A61F 13/15593; B05D 1/26; B05D 1/265; B29L 2031/4878
USPC .... 156/60, 62.2, 91, 92, 150, 151, 153, 154, 156/242, 245, 272.2, 272.8, 278, 290, 156/291, 292, 297, 298, 308.2, 308.4, 156/349, 500, 538, 543, 546, 578; 118/45, 200, 209, 211, 216, 221, 225, 118/226, 235, 410, 411, 419; 204/192.16; 384/625; 51/309; 428/697, 428/698, 699; 29/460, 428, 527.1, 527.2, 29/527.3; 427/356, 357, 358
See application file for complete search history.

(56) References Cited

U.S. PATENT DOCUMENTS

| | | | |
|---|---|---|---|
| 4,463,045 A | 7/1984 | Ahr et al. | |
| 4,493,868 A | 1/1985 | Meitner | |
| 4,556,146 A | 12/1985 | Swanson et al. | |
| 4,589,876 A | 5/1986 | Van Tilburg | |
| 4,687,478 A | 8/1987 | Van Tilburg | |
| 4,735,169 A | 4/1988 | Clawston et al. | |
| 4,844,004 A | 7/1989 | Hadzimihalis et al. | |
| 4,854,984 A | 8/1989 | Ball et al. | |
| 4,950,264 A | 8/1990 | Osborn, III | |
| 5,009,653 A | 4/1991 | Osborn, III | |
| 5,267,992 A | 12/1993 | Van Tilburg | |
| 5,421,085 A * | 6/1995 | Muscato | B05C 5/0254 29/890.1 |
| 5,620,779 A | 4/1997 | Levy et al. | |
| 5,798,167 A | 8/1998 | Connor et al. | |
| 6,004,893 A | 12/1999 | Van Tilburg | |
| 6,244,148 B1 | 6/2001 | Vees | |
| 6,248,195 B1 | 6/2001 | Schmitz | |
| 7,056,386 B2 | 6/2006 | Pahl | |
| 7,777,094 B2 | 8/2010 | Mori et al. | |
| 7,861,756 B2 | 1/2011 | Jenquin et al. | |
| 8,186,296 B2 | 5/2012 | Brown et al. | |
| 8,347,809 B2 | 1/2013 | Takahashi et al. | |
| 8,399,053 B2 | 3/2013 | Bondeson et al. | |
| 8,440,043 B1 | 5/2013 | Schneider et al. | |
| 8,979,521 B2 | 3/2015 | Kondo | |
| 9,248,054 B2 | 2/2016 | Brown et al. | |
| 9,265,672 B2 | 2/2016 | Brown et al. | |
| 9,295,590 B2 | 3/2016 | Brown et al. | |
| 2007/0142798 A1 | 6/2007 | Goodlander et al. | |
| 2007/0142806 A1 | 6/2007 | Roe et al. | |
| 2007/0287983 A1 | 12/2007 | Lodge et al. | |
| 2008/0124531 A1* | 5/2008 | Hanyu | B23C 5/1009 428/216 |
| 2010/0028636 A1* | 2/2010 | Vetter | C23C 14/024 428/213 |
| 2012/0111975 A1* | 5/2012 | Ogasawara | B05C 5/025 239/589 |
| 2012/0219657 A1 | 8/2012 | Kondo | |
| 2013/0049438 A1 | 2/2013 | Nootbaar et al. | |
| 2013/0213547 A1 | 8/2013 | Schneider et al. | |
| 2013/0218116 A1 | 8/2013 | Schneider | |
| 2014/0377506 A1 | 12/2014 | Eckstein et al. | |
| 2014/0377513 A1 | 12/2014 | Galie et al. | |

* cited by examiner

NOZZLE ASSEMBLY USED TO MANUFACTURE ABSORBENT ARTICLES

FIELD

The present disclosure relates to apparatuses and methods for manufacturing absorbent articles, and more particularly, slot nozzles having a body constructed from a first material with abrasion resistant material fused to the body, wherein the abrasion resistant material is different from the first material.

BACKGROUND

Along an assembly line, various types of articles, such as for example, diapers and other absorbent articles, may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheet, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

Various methods and apparatuses may be used for forming and/or attaching different components to an advancing web and/or otherwise modify an advancing web during the manufacturing process. For example, some operations may utilize a slot nozzle to deposit a fluid onto an advancing substrate. As such, a continuous web may advance in a machine direction adjacent the slot nozzle. A portion of the slot nozzle contacts the advancing substrate as the fluid is deposited on the advancing substrate. Repetitive contact between the substrate and the slot nozzle and/or the properties of the fluid expelled from the slot nozzle causes wear on the slot nozzle. This wear necessitates repair or replacement, which may be relatively costly, of the slot nozzle.

Consequently, it would be beneficial to provide methods and apparatuses with slot nozzles that are less susceptible to localized wear and where the slot nozzles may be designed for ease of manufacture at relatively low costs.

SUMMARY

Aspects of the present disclosure involve apparatuses and methods for manufacturing absorbent articles, and more particularly, apparatuses and methods for applying fluid to an advancing substrate during the manufacture of disposable absorbent articles.

In one embodiment, an apparatus for applying fluid to an advancing substrate may include a nozzle body including a first material. The first material may be selected from the group consisting of: an iron based alloy, an aluminum based alloy, and a titanium based alloy. The nozzle body may also include a passageway and one or more abrasion resistant materials fused to the nozzle body to form a nozzle contact portion. The nozzle contact portion may be adapted to contact the advancing substrate and/or the fluid. Further, the one or more abrasion resistant materials may be different from the first material. The apparatus may also include a shim plate connected with the nozzle body. The shim plate may include a plurality of slots in fluid communication with the passageway.

In one embodiment, a method for making an apparatus for applying fluid to an advancing substrate may include: providing a nozzle body consisting of a first material, wherein the first material is selected from the group consisting of: an iron based alloy, an aluminum based alloy, and a titanium based alloy, and wherein the body comprises an outer circumferential surface; forming a portion of an outer surface of the nozzle body to define a recessed area; filling the recessed area with one or more abrasion resistant materials, the one or more abrasion resistant materials being different from the first material; and fusing the one or more abrasion resistant materials to the nozzle body in the recessed area.

In one embodiment, a method for restoring an apparatus for applying fluid to an advancing substrate may include: providing a nozzle body comprising an outer surface, the nozzle body consisting of a first material, wherein the first material is selected from the group consisting of: an iron based alloy, an aluminum based alloy, and a titanium based alloy, and wherein the body comprises an outer circumferential surface; advancing a substrate in contact with the outer surface of the nozzle body; removing a portion of the outer surface of the nozzle body with the advancing substrate to define a recessed area; filling the recessed area with one or more abrasion resistant materials, the one or more abrasion resistant materials being different from the first material; and fusing the one or more abrasion resistant materials to the nozzle body in the recessed area.

DETAILED DESCRIPTION

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The present disclosure relates to apparatuses and methods for manufacturing absorbent articles, and more particularly, a nozzle assembly that may be used to dispense a fluid onto a traversing substrate. The nozzle assembly may be configured to extrude a fluid onto a substrate in a film-like or strip-like manner. More specifically, the nozzle body comprises a passageway through which a fluid may pass such that the fluid may be deposited onto the traversing substrate. A shim plate may also be connected with the nozzle body. The shim plate may be in fluid communication with the passageway. The shim plate may include a plurality of slots through which fluid may pass prior to being deposited on the traversing substrate. The traversing substrate may contact a portion of the nozzle body as fluid is deposited thereon. The traversing substrate and/or the fluid applied to the traversing substrate may result in wear of a portion of the nozzle body. Thus, one or more abrasion resistant materials may be fused to the nozzle body to form an outer surface adapted to contact the advancing substrate and/or the fluid as it is extruded. The nozzle body may be made from a first material and the one or more abrasion resistant materials may be made from a material that is different than the first material. Having the nozzle body and the abrasion resistant materials be different, allows for the first material of the nozzle body to be selected based on criteria separate from abrasion resistance, such as cost, thermal capabilities, ease of manufacture, and the like. Similarly, the abrasion resistant material may be selected based on criteria specific to the type of fluid to be dispensed, the substrate properties, abrasion resistance, and the like. Due to the relatively small amount of abrasive material fused to the nozzle body, cost becomes relatively less of a factor, which is important for producing cost-competitive products, such as absorbent articles. Further, the manufacture and maintenance of the nozzle body may be optimized. As discussed in more detail below, the abrasion resistant material is formed on and fused to the nozzle body as opposed to requiring new fabrication of the nozzle body and/or various additional materials being fastened thereto. Thus, some of the difficulties associated with current slot nozzle manufacturing techniques may be alleviated.

Figure 1:
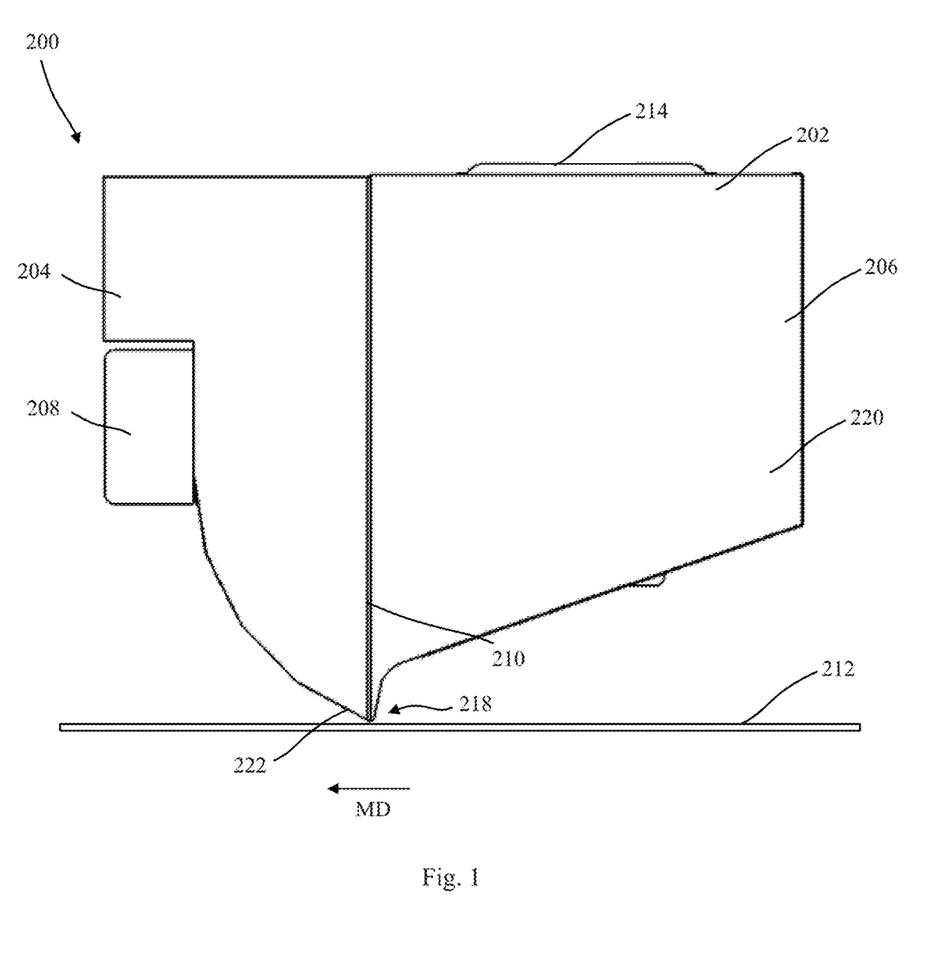
FIG. 1 is an end view of a nozzle assembly.
Figure 2:
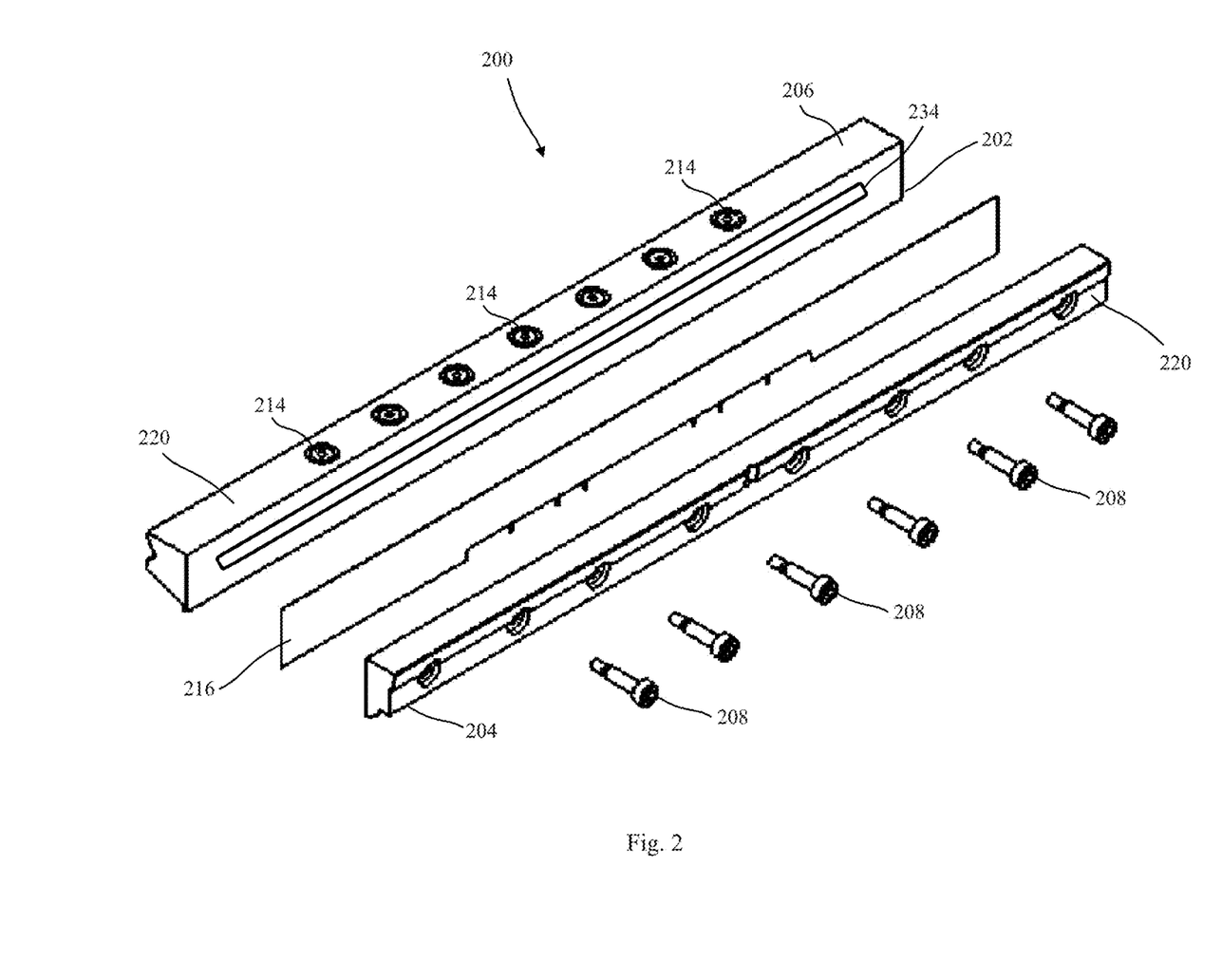
FIG. 2 is an exploded view of a nozzle assembly.

It is to be appreciated the nozzle assembly herein may be configured in various ways. For example, FIG. 1 shows an end view of a configuration of a nozzle assembly 200 including a nozzle body 202. The nozzle body 202 may be a single nozzle member, or the nozzle body 202 may include more than one nozzle member. For example, as shown in FIGS. 1 and 2, the nozzle body 202 includes a first nozzle member 204 and a second nozzle member 206. The first nozzle member 204 may be removably connected with the second nozzle member 206. In some embodiments, the first nozzle member 204 may be removably connected with the second nozzle member 206 with one or more screws 208. It is to be appreciated that the first nozzle member 204 also may be removably connected to the second nozzle member 206 with another mechanical connection device such as pins, clasps, nails, or the like. As illustrated in FIG. 1, a portion of the first nozzle member 204 may be in facing relationship with the second nozzle member 206. The first nozzle member 204 may be positioned with respect to the second nozzle member 206 such that a gap 210 is present between the first nozzle member 204 and the second nozzle member 206.

The gap 210 may be wide enough such that a fluid may pass between the first nozzle member 204 and the second nozzle member 206. A fluid may flow to either or both of the first nozzle member 204 and the second nozzle member 206, into the gap 210, and onto an advancing substrate 212. As illustrated in FIG. 1, the nozzle body 202 may include a fluid orifice 214. A fluid may enter the nozzle body 202 through the fluid orifice 214. The fluid may traverse through one or more passageways defined by the nozzle body and be deposited on the advancing substrate 212.

It is to be appreciated that the nozzle body 202 may be directly or indirectly, removably connected to another device. For example, in some embodiments, an adapter may be used to connect the nozzle body to another device.

Further, a shim plate 216, as illustrated in FIG. 2, may be positioned between the first nozzle member 204 and the second nozzle member 206. The shim plate 216 may be positioned in the gap 210 between the first nozzle member 204 and the second nozzle member 206. Further, a first side of the shim plate 216 may abut the first nozzle member 204 and a second side of the shim plate 216 may abut the second nozzle member 206. The shim plate 216 may include a plurality of fluid slots. The plurality of fluid slots may be in fluid communication with a passageway 234 defined by at least one of the first nozzle member 204 and the second nozzle member 206. The passageway 234 may extend across the face of one of the first nozzle member 204 or the second nozzle member 206. The fluid may then traverse through the passageway 234 and into the fluid slots of the shim plate 216. The fluid may then be deposited onto an advancing substrate via the shim plate 216. A single shim plate or multiple shim plates may be positioned between the first nozzle member and the second nozzle member. The additional shim plates allow for relatively greater customization of the pattern in which the fluid is applied to the substrate.

Figure 3:
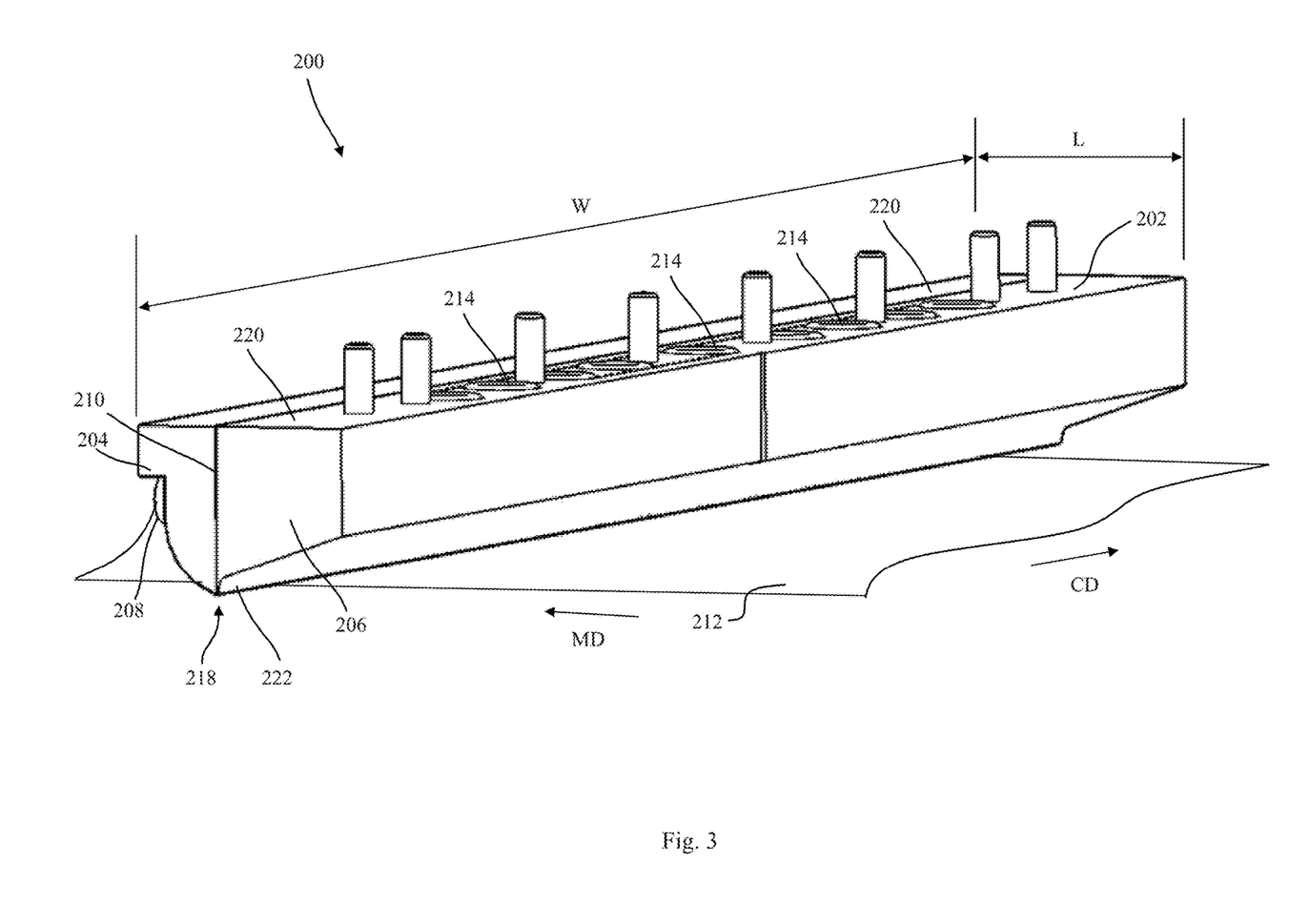
FIG. 3 is an isometric view of a nozzle assembly and an advancing substrate.

The substrate 216 may advance in a machine direction MD and traverse past a portion of the nozzle body 202, as illustrated in FIG. 3. The nozzle body 202 has a width W, which is in a direction parallel to the cross direction CD, and a length L, which is parallel to the machine direction MD. The nozzle body 202 may have a width W sufficient to cover the intended portion of the substrate 212 with fluid. For example, as illustrated in FIG. 3, the nozzle body 202 has a width W that extends beyond the outer edges of the substrate 212. It is also to be appreciated that the width W of the nozzle body 202 may be less than the width of the substrate. As the substrate 212 advances past the nozzle body 202 a fluid may be deposited onto the substrate 212. Further the substrate 212 may engage a portion of the nozzle body 202 as it traverses in the machine direction MD. More specifically, the nozzle body 202 may include a nozzle contact portion 218, which is an outer surface of the nozzle body. The nozzle contact portion 218 may differ based on how the substrate 216 interacts with the nozzle body 202. The nozzle contact portion 218 is the portion of the nozzle body 202 that undergoes wear due to the constant or intermittent contact with the substrate 216 and/or the fluid excreted by the nozzle body 202. It is also to be appreciated that the wear may be due, at least in part, to the device used to advance the substrate past the nozzle body, such as a rotating drum or a conveyor. The wear leads to relatively frequent replacement of the nozzle body 202, which becomes costly for manufacturers. To minimize cost and reduce the wear on the nozzle contact portion 218, a material may be fused thereto. Fusing a material to the nozzle contact portion 218 allows the nozzle contact portion 218 to be replaced independent of the remainder of the nozzle body 202.

The material fused to the nozzle contact portion 218 may be an abrasion resistant material 222. The abrasion resistant material 222 may be fused to the nozzle contact portion 218 or on any external surface of the nozzle body 202 to prevent wear. The abrasion resistant material 222 may include one or more different materials. Further, the abrasion resistant material 222 may be applied to the nozzle body 202 in one or more layers. The abrasion resistant material may be different than the first material 220 of the nozzle body 202. Thus, the first material 220 of the nozzle body 202 may be a more cost effective material than the abrasion resistant material. Further, the first material 220 of the nozzle body 202 may also be selected for ease of manufacture, whereas, the abrasion resistant material may or may not be suited for the ease of manufacture of the nozzle body 202. Using at least two different materials allows manufacturers to select the best material for the specific component, while also satisfying cost restraints, ease of manufacture, and optimum material properties. Using at least two different materials to form a part may be referred to as forming a hybrid part.

As previously mentioned, the first material 220 of the nozzle body 202 is different from the one or more abrasion resistant materials 220 fused thereto. It is to be appreciated that the first material 220 may be various types of materials, such as various types of metallic materials. For example, in some configurations, the first material 220 is selected from the group consisting of: an iron based alloy, an aluminum based alloy, and a titanium based alloy. In some configurations, the iron based alloy is selected from the group consisting of: stainless steel and tool steel. In some configurations, the first material is a hot-working tool steel or a tool steel, such as for example, X37CrMoVS-1 steel. It is also to be appreciated that the one or more abrasion resistant materials 222 may be various types of materials. For example, the one or more abrasion resistant materials 222 may include at least one of: powder-metallurgical steel; titanium carbide, niobium carbide, tantalum carbide, chromium carbide, tungsten carbide, and mixtures thereof. The abrasion resistant material 222 may include a carbide of at least one element of the fourth, the fifth, the sixth and/or the seventh group of the periodic table. Carbides from the fourth group may be titanium carbide, zirconium carbide, hafnium carbide or a mixture thereof. Carbides from the fifth group may be vanadium carbide, niobium carbide, tantalum carbide or a mixture thereof. Carbides from the sixth group may be chromium carbide, molybdenum carbide, tungsten carbide or a mixture thereof. Carbides from the seventh group may be manganese carbide, rhenium carbide or a mixture thereof. Carbides of several groups can be used individually or as a mixture. In one embodiment, titanium carbide, niobium carbide, tantalum carbide, chromium carbide, tungsten carbide or a mixture thereof is used. The carbides may be deposited as a powder comprising particles of several sizes and/or shapes. For example, in some embodiments, the particles may be from about 40 µm to about 90 µm. Carbides may be provided in a matrix material, wherein matrix material may comprise nickel, cobalt and/or iron. The carbides may be present in the matrix material in an amount of from about 60% to about 80%, in another embodiment in an amount of from about 70% to about 80%, in yet another embodiment in an amount of from about 70% to about 75% or in yet another embodiment any individual number within the values provided or in any range including or within the values provided. It is also to be appreciated that high speed steel may also be used as an abrasion resistant material.

When assembling the nozzle body 202 herein, the first material 220 may be formed into a generally block-shaped forging. The forging may be machined or otherwise worked to form the nozzle body 202. For example, the forging may be worked or machined into the nozzle body 202 so as to include various features, such as holes, passageways, a nozzle contact portion with specific geometry, and inlet orifices, for example.

Figure 4A:
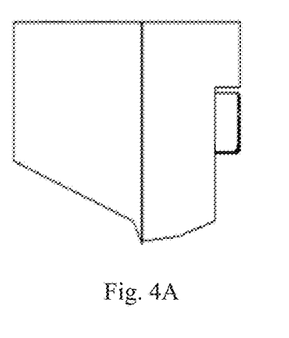
FIG. 4A is a side view of a nozzle assembly.
Figure 4B:
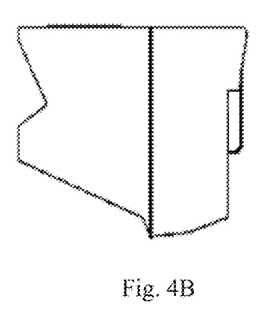
FIG. 4B is a side view of a nozzle assembly.
Figure 4C:
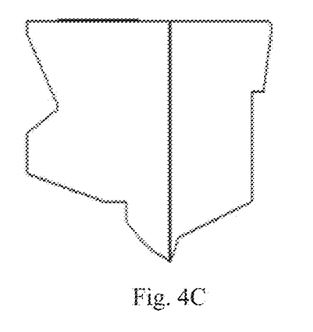
FIG. 4C is a side view of a nozzle assembly.
Figure 4D:
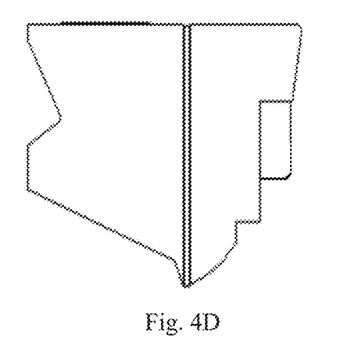
FIG. 4D is a side view of a nozzle assembly.
Figure 4E:
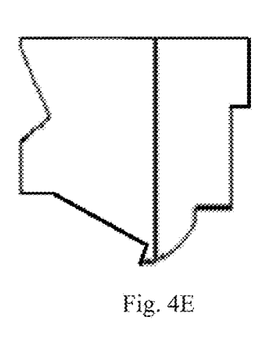
FIG. 4E is a side view of a nozzle assembly.
Figure 5A:
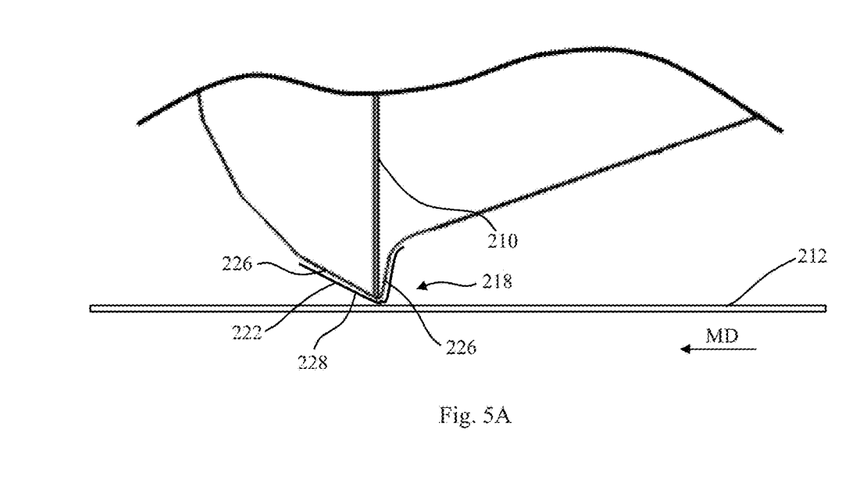
FIG. 5A is a partial side view of a nozzle assembly.
Figure 5B:
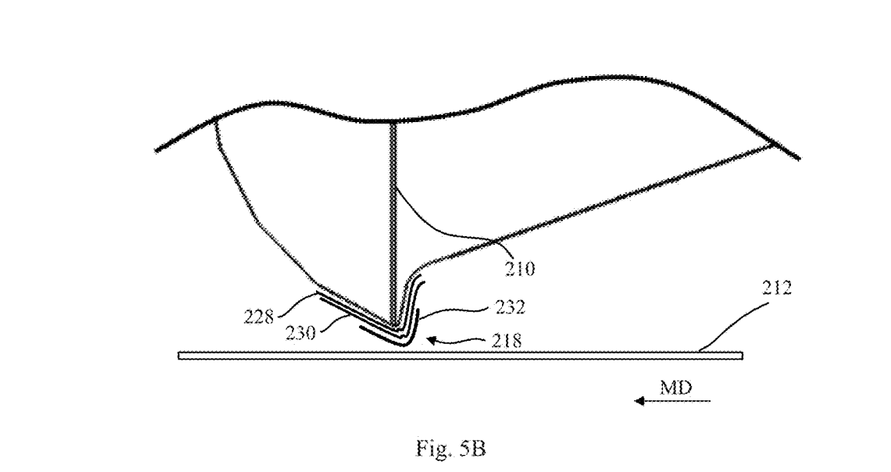
FIG. 5B is a partial side view of a nozzle assembly.
Figure 5C:
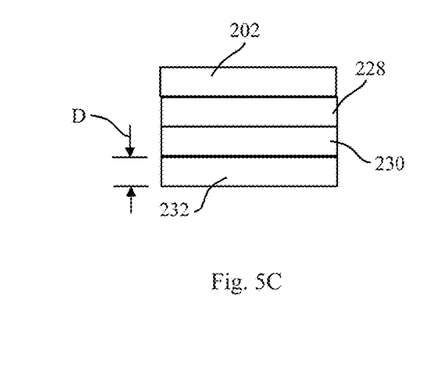
FIG. 5C is a schematic representation of the layers of abrasion resistant material applied to the nozzle body.

It is to be appreciated that the nozzle contact portion 218 may have various shapes and sizes, as illustrated, for example, in FIGS. 4A-4E. The shape and size of the nozzle contact portion 218 may depend, in part, on the fluid to be excreted from the nozzle body 202 and the material that is to be processed. Each nozzle contact portion 218 may include a base surface 226, as illustrated in FIG. 5A. As discussed in more detail below, the abrasion resistant material 222 is deposited onto the base surface 226 nozzle contact portion 218 to form a first layer 228 of abrasion resistant material 222, as shown for example in FIG. 5A. More particularly, the abrasion resistant material 222 is fused to first material 220 of the nozzle body 202 without having to otherwise fasten additional components of material to the nozzle body. As such, the assembly 200 herein may not require extensive machining of abrasion resistant materials and/or require assembly operations of fastening discrete components made of abrasion resistant materials to the nozzle body.

As previously mentioned, one or more abrasion resistant materials 222 are fused to the nozzle body 202 in the nozzle contact portion 218. And in some configurations, one or more abrasion resistant material 222 may be fused to the nozzle body 202 with a laser metal deposition process, such as disclosed in U.S. Patent Publication No. 2013/0049438 A1. The laser may operate out of focus in a range of from about 0.1 mm to several centimeters. During the laser deposition process, the first material 220 of the nozzle body 202 may be partially melted during deposition of the abrasion resistant material 222 onto the nozzle contact portion 218. As such, a metallurgic bond may be created between the abrasion resistant material 222 and the first material 220 of the nozzle body 202. As used herein, a "metallurgical bond" means that the abrasion resistant material is fused to the first material of the body such that the microstructure of the first material may be intimately linked to the microstructure of the abrasion resistant material. In some configurations when applying more than one abrasion resistant material, metallurgic bonds also may be created between the different abrasion resistant materials. It is also to be appreciated that, in some embodiments, the nozzle body may remain substantially unmelted, and thus, the nozzle body may stay substantially in its condition pre-laser deposition. This may be advantageous to minimize the heat affected zone. Minimizing the heat affected zone of the nozzle body, for example, may lead to a relatively reduced number of cracks and a more resilient nozzle body.

In some configurations, the abrasion resistant material may include multiple layers of material that are applied to the nozzle body 202, such as disclosed in U.S. Patent Publication No. 2013/0049438 A1. For example, the abrasion resistant material may include a first layer 228, a second layer 230, and a third layer 232, as illustrated in FIGS. 4B and 4C. The first layer 228 may be referred to as a bonding layer, the second layer 230 may be referred to as a bearing layer, and the third layer 232 may be referred to as a wear resistant layer. The bonding layer may be applied to the nozzle body 202; the bearing layer may be applied to the bonding layer; and the wear resistant layer may be applied to the bearing layer. Thus, the first layer 228 or bonding layer may provide a metallurgical bond to the nozzle body 202 when applied by a laser deposition process. As such, the bonding layer may be a metal alloy that is similar to the first material 220 of the nozzle body 202, which in turn, may form little or no brittle phase when mixed with the first material 220. The second layer 230 or bearing layer may be configured to provide sufficient strength, such as compressive strength, and stiffness when the wear resistant layer is loaded during operation. Thus, the second layer or bearing layers may be a metallic alloy that is similar to the bonding layer but contains elements to form solid solutions and/or medium hard phases. The third layer 232 or wear resistant layer may be a compound of a matrix in which hard phases, such as for example carbides, borides and/or nitrides, are embedded. The matrix may be a metallic alloy which is similar to the bearing layer but also contains elements to form a solid solution and/or medium hard phases, and also be identical with the bearing layer. The hard phases may be homogeneously distributed inside the metallic matrix in various amounts. The hard phases may also be incorporated as solid particles during the coating process or may precipitate during the solidification process from the melt.

It is to be appreciated that any number of layers of abrasion resistant material may be applied to the nozzle contact portion. For example, a single layer, two layers, three layers, four layers, and/or 5 layers may be applied to the nozzle contact portion. Further, not all layers have to completely cover the nozzle contact portion. For examples, as illustrated in FIG. 4B, a first layer 228 may be applied to a certain portion of the nozzle contact portion. A second layers 230 may be applied to the first layer in substantially the same area of the nozzle contact portion. Further, a third layer 232 may be applied such that only a portion of the second layer is covered. The area of application may depend upon the substrate and the fluid to be dispensed. The additional layers of abrasion resistant material may lead to increased hardness of the nozzle contact portion 218. Further, it may be beneficial to only cover a portion due to the type of wear that occurs. For example, the portion of the nozzle contact portion that first engages or initially contacts the substrate may incur more wear than a portion downstream of the initial contact area and, thus, may need more layers of abrasion resistant material. By contrast, the downstream portion of the initial contact area may have fewer layers. This selective application may be a cost savings to manufacturers.

Further, the abrasion resistant materials may be applied at various depths D. The depth D of the abrasion resistant material is measured perpendicular to the surface on which it is applied. For example, a layer of abrasion resistant material may be applied at a depth of from about 0.1 mm to about 4.5 mm and/or from about 0.5 mm to about 4.0 mm and/or from about 1.0 mm to about 3.5 mm, specifically reciting all 0.1 mm increments within the specified ranges and all ranges formed therein and thereby. Each layer of abrasion resistant material may have a different depth or each layer of abrasion resistant materials may have the same depth.

It is also to be appreciated that only one of the first nozzle member 204 or the second nozzle member 206 may be worn during processing. If only of the nozzle members are worn, the abrasion resistant material need only be applied to the nozzle member that experiences wear. Thus, either the first nozzle member 204 or the second nozzle member 206 may be free of abrasion resistant material.

The process for applying fluid to the advancing substrate may include, for example, providing a nozzle body made from at least a first material. The first material, as previous discussed, may be an iron based alloy, an aluminum based alloy, or a titanium based alloy. The nozzle body may include a nozzle contact portion or a portion of the nozzle body that experiences wear due to the interaction of the nozzle body with the substrate or the fluid. To prevent wear of the nozzle body and, more specifically, the nozzle contact portion, a laser deposition process may be used to deposit one or more abrasion resistant materials onto the nozzle body. The laser deposition process may form a surface of the nozzle body onto which the abrasion resistant material may be deposited. For example, in some embodiments, the first layer may be a nickel based alloy. The abrasion resistant material is different than the first material of the nozzle body. Additional layers of abrasion resistant materials may be added. For example, in some embodiments, multiple layers of Vanadium carbide are fused to the nozzle body with the laser. It is to be appreciated that recesses may be placed in the nozzle body to aid in having the abrasion resistant material adhere to the nozzle body. Further, the abrasion resistant material may be applied to the nozzle body in various forms. For example, the abrasion resistant material may be powder prior to being fused to the nozzle body.

As previously described, the addition of the abrasion resistant material to the nozzle body may aid in maintaining the nozzle body. More specifically, when the nozzle body becomes worn due to processing, the whole nozzle body does not need to be replaced. Rather, the abrasion resistant material need only be replaced. The nozzle body may be machined and additional abrasion resistant material may be applied to the nozzle body. The process for restoring the nozzle body may include, having a nozzle body made from a first material and including a nozzle contact portion. As previously discussed, a substrate may advance in the machine direction and may engage the nozzle contact portion of the nozzle body. Further, the fluid dispensed by the nozzle body may interact with the nozzle contact portion of the nozzle body. Wear may develop as the substrate and fluid contact the nozzle body. Thus, due to the wear, a portion of the nozzle body may be removed. More specifically, the abrasion resistant material in the nozzle contact portion may be worn away during processing. This may create a recess or void that needs to be filled with additional abrasion resistant material so that processing may continue. The recess or void is filed with one or more abrasion resistant materials. The abrasion resistant materials are different that the first material. The abrasion resistant materials may be fused by using a laser, for example. Using an abrasion resistant material may extend the life of the nozzle body.

It is to be appreciated that the substrate 212 may advance from the nozzle assembly to additional converting operations, such as for example, cutting, embossing, and bonding.

Figure 6:
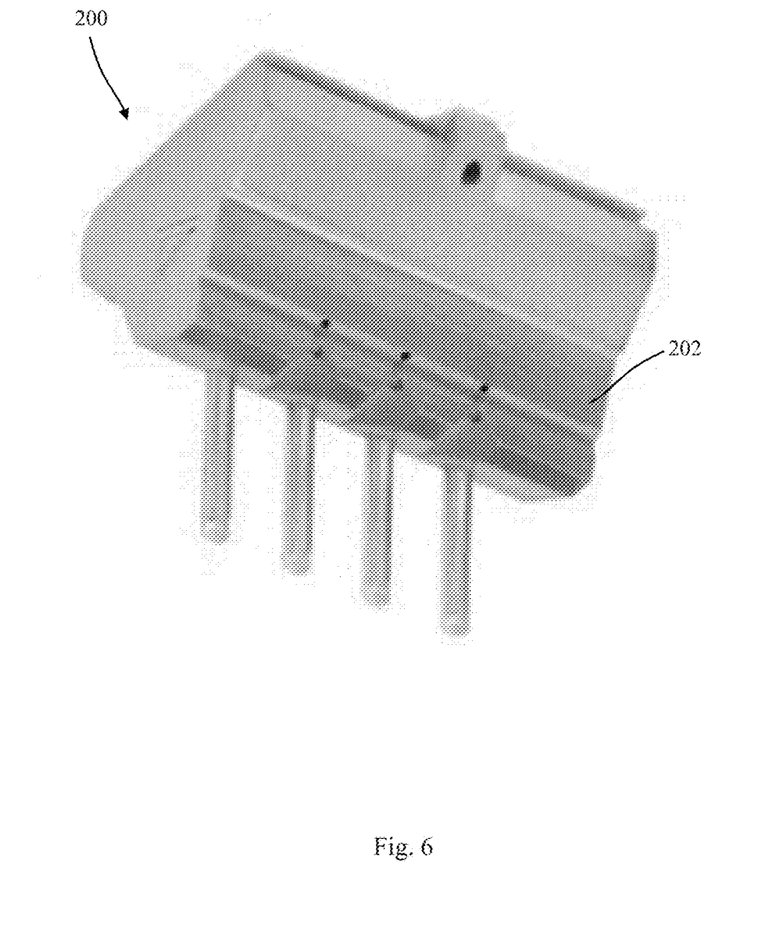
FIG. 6 is an isometric view of a nozzle assembly.

It is also to be appreciated that material other than a substrate may advance past the nozzle body such that the nozzle body deposits fluid onto the material. For example, a nozzle assembly may be used to deposit fluid onto elastic strands. Further, in some embodiments, as illustrated in FIG. 6, the nozzle assembly may be configured as a single nozzle body having no shim. The aforementioned disclosure regarding the laser deposition of one or more abrasion resistant materials may also be used in the nozzle assembly as illustrated in FIG. 6.

Figure 7A:
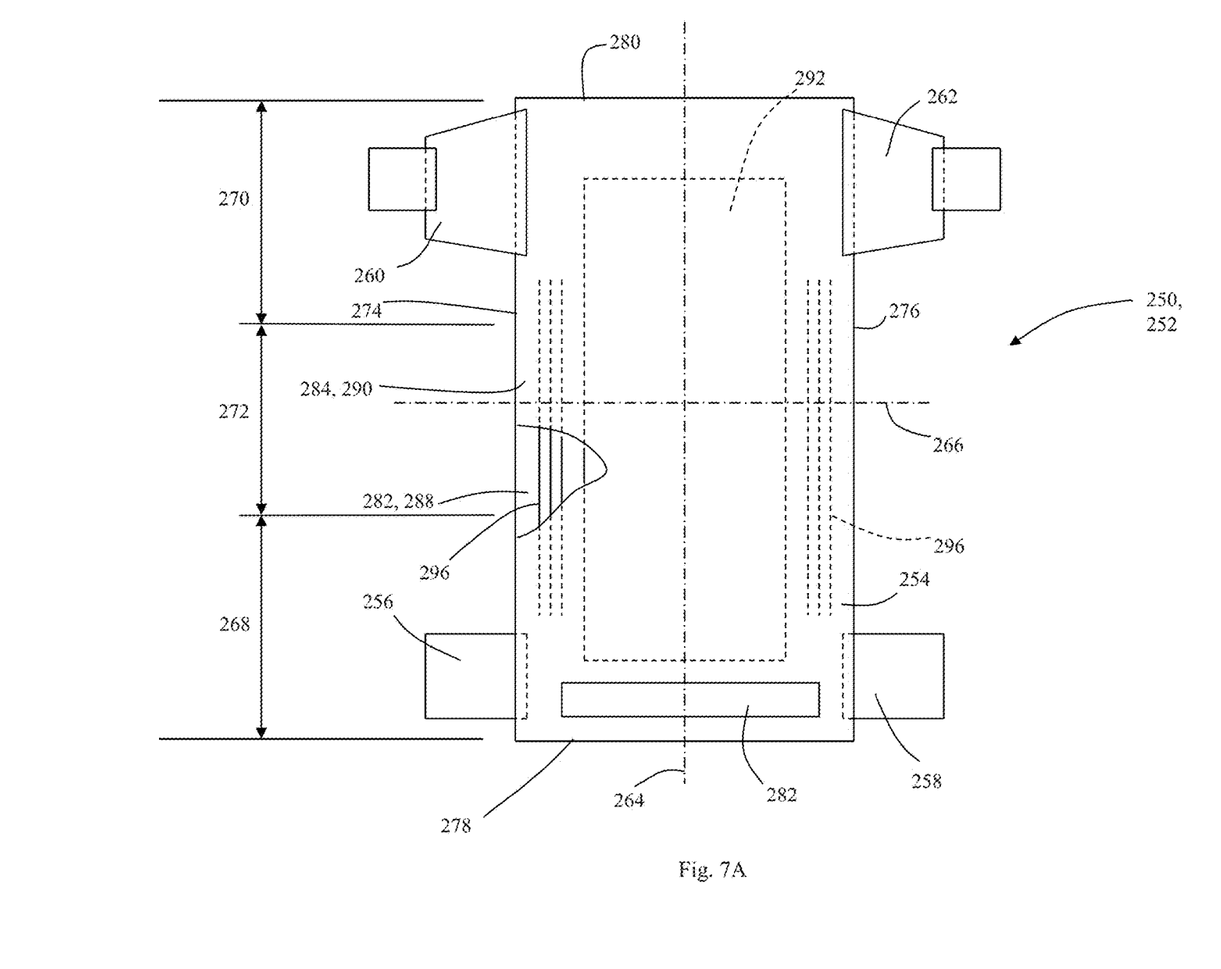
FIG. 7A is a partially cut away plan view of an absorbent article in the form of a taped diaper that may include one or more substrates and components manipulated during manufacture according to the apparatuses and methods disclosed herein with the portion of the diaper that faces away from a wearer oriented towards the viewer.
Figure 7B:
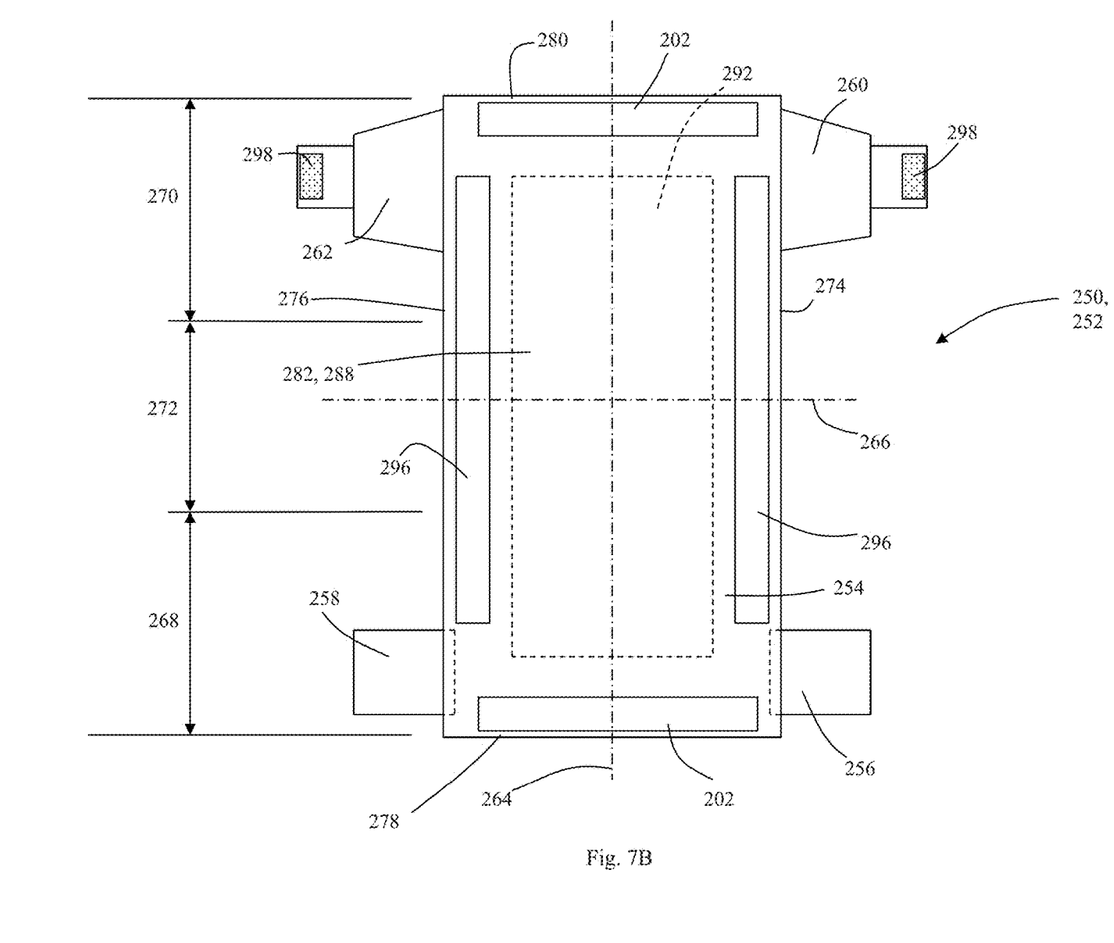
FIG. 7B is a plan view of the absorbent article of FIG. 7A that may include one or more substrates and components manipulated during manufacture according to the apparatuses and methods disclosed herein with the portion of the diaper that faces toward a wearer oriented towards the viewer.

As mentioned above, apparatuses and methods of the present disclosure may be utilized to perform various manufacturing operations on substrates used in the manufacture of absorbent articles. Such substrates may be utilized in absorbent article components such as, for example: backsheets, topsheets, absorbent cores, front and/or back ears, fastener components, and various types of elastic webs and components such as leg elastics, barrier leg cuff elastics, and waist elastics. For the purposes of a specific illustration, FIGS. 7A and 7B show an example of a disposable absorbent article 250 in the form of a diaper 252 that may be constructed from such substrates and components manipulated during manufacture according to the apparatuses and methods disclosed herein. In particular, FIG. 7A is a partially cut away plan view of an absorbent article in the form of a taped diaper that may include one or more substrates and components manipulated during manufacture according to the apparatuses and methods disclosed herein with the portion of the diaper that faces away from a wearer oriented towards the viewer. FIG. 7B is a plan view of the absorbent article of FIG. 7A that may include one or more substrates and components manipulated during manufacture according to the apparatuses and methods disclosed herein with the portion of the diaper that faces toward a wearer oriented towards the viewer.

As shown in FIGS. 7A-7B, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIGS. 7A-7B, the chassis 254 includes an inner, body-facing surface 282, and an outer, garment-facing surface 284. A portion of the chassis structure is cut-away in FIGS. 7A-7B to more clearly show the construction of and various features that may be included in the diaper. As shown in FIGS. 7A-7B, the chassis 254 of the diaper 252 may include a topsheet 288 defining the inner, body-facing surface 282, and a backsheet 290 defining the outer, garment-facing surface 284. An absorbent core 292 may be disposed between a portion of the topsheet 288 and the backsheet 290. As discussed in more detail below, any one or more of the regions may be stretchable and may include an elastomeric material or laminate as described herein. As such, the diaper 252 may be configured to adapt to a specific wearer's anatomy upon application and to maintain coordination with the wearer's anatomy during wear.

The absorbent article 250 may also include an elastic waist feature 202 shown in FIGS. 7A-7B in the form of a waist band and may provide improved fit and waste containment. The elastic waist feature 202 may be configured to elastically expand and contract to dynamically fit the wearer's waist. The elastic waist feature 202 can be incorporated into the diaper and may extend at least longitudinally outwardly from the absorbent core 292 and generally form at least a portion of the first and/or second outer edges 278, 280 of the diaper 252. In addition, the elastic waist feature may extend laterally to include the ears. While the elastic waist feature 202 or any constituent elements thereof may comprise one or more separate elements affixed to the diaper, the elastic waist feature may be constructed as an extension of other elements of the diaper, such as the backsheet 290, the topsheet 288, or both the backsheet and the topsheet. In addition, the elastic waist feature 202 may be disposed on the outer, garment-facing surface 284 of the chassis 254; the inner, body-facing surface 282; or between the inner and outer facing surfaces. The elastic waist feature 202 may be constructed in a number of different configurations including those described in U.S. Patent Publication Nos. 2007/0142806 A1; 2007/0142798 A1; and 2007/0287983 A1, all of which are hereby incorporated by reference herein.

As shown in FIGS. 7A-7B, the diaper 252 may include leg cuffs 296 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 296 may be disposed in various ways on the diaper 202.

The diaper 252 may be provided in the form of a pant-type diaper or may alternatively be provided with a re-closable fastening system, which may include fastener elements in various locations to help secure the diaper in position on the wearer. For example, fastener elements 298 may be located on the ears and may be adapted to releasably connect with one or more corresponding fastening elements located in the first or second waist regions. For example, as shown in FIG. 7A, the diaper 252 may include a connection zone 282, sometimes referred to as a landing zone, in the first waist region 268. It is to be appreciated that various types of fastening elements may be used with the diaper.

It is to be appreciated that the apparatuses and methods herein may be used to provide for the cutting and removal of trim material from advancing substrates and components during the manufacture of absorbent articles, such as the diaper of FIGS. 7A-7B. For example, the trim removal apparatus may be used to remove trim material during the manufacture of a topsheet, a backsheet, an absorbent core, an ear, and fastening elements.

EXAMPLES

A. An apparatus for applying fluid to an advancing substrate, the apparatus comprising: a nozzle body comprising a first material, wherein the first material is selected from the group consisting of: an iron based alloy, an aluminum based alloy, and a titanium based alloy, and wherein the nozzle body comprises: a passageway; one or more abrasion resistant materials fused to the nozzle body to form a nozzle contact portion adapted to contact the advancing substrate, the one or more abrasion resistant materials being different from the first material; and a shim plate connected with the nozzle body, the shim plate comprising a plurality of slots in fluid communication with the passageway.

B. The apparatus according to paragraph A, wherein the nozzle body comprises a first nozzle member; and a second nozzle member removably connected with the first nozzle member.

C. The apparatus according to paragraph B, wherein the shim plate is positioned between the first nozzle member and the second nozzle member.

D. The apparatus according to any one of paragraphs A-C, wherein the one or more abrasion resistant materials comprises at least one of: powder-metallurgical steel; titanium carbide, niobium carbide, tantalum carbide, chromium carbide, tungsten carbide, and a carbide of at least one element of the fourth, the fifth, the sixth and/or the seventh group of the periodic table.

E. The apparatus according to any one of paragraphs A-D, wherein the iron based alloy is selected from the group consisting of: stainless steel and tool steel.

F. The apparatus according to any one of paragraphs A-D, wherein the abrasion resistant material comprises a depth of from about 0.5 mm and less than about 4 mm.

G. The apparatus of claim 1, wherein the one or more abrasion resistant materials comprises a first abrasion resistant material and a second abrasion resistant material.

H. The apparatus according to paragraph G, wherein the first abrasion resistant material is different than the second abrasion resistant material.

I. The apparatus according to paragraph G, wherein at least a portion of the first abrasion resistant material is positioned adjacent to the nozzle body and between the second abrasion resistant material and the nozzle body.

J. The apparatus according to paragraph B, wherein the first nozzle member or the second nozzle member is free of abrasion resistant material.

K. The apparatus according to paragraph B, wherein at least one of the first nozzle member and the second nozzle member comprises a nozzle contact portion.

L. A method for making an apparatus for applying fluid to an advancing substrate, the method comprising: providing a nozzle body consisting of a first material, wherein the first material is selected from the group consisting of: an iron based alloy, an aluminum based alloy, and a titanium based alloy, and wherein the body comprises an outer circumferential surface; forming a portion of an outer surface of the nozzle body to define a recessed area; filling the recessed area with one or more abrasion resistant materials, the one or more abrasion resistant materials being different from the first material; and fusing the one or more abrasion resistant materials to the nozzle body in the recessed area.

M. The method according to paragraph L, wherein fusing further comprises applying the one or more abrasion resistant materials by a laser deposition process.

N. The method according to any one of paragraphs L-M, wherein the abrasion resistant material is applied to the recessed area as a powder.

O. The method according to any one of paragraphs L-N, wherein the abrasion resistant material is applied to the recess as a first layer.

P. The method according to any one of paragraphs L-O, wherein a laser is used to apply the abrasion resistant material to the recessed area of the nozzle body.

Q. The method according to paragraph M, wherein a portion of the nozzle body is minimally melted during the laser deposition process.

R. The method according to paragraph O, wherein a second layer of abrasion resistant material is applied to the first layer of abrasion resistant material, and wherein the first layer of abrasion resistant material is partially melted when the second layer of abrasion resistant material is applied to the nozzle body by laser deposition.

S. A method for restoring an apparatus for applying fluid to an advancing substrate, the method comprising: providing a nozzle body comprising an outer surface, the nozzle body consisting of a first material, wherein the first material is selected from the group consisting of: an iron based alloy, an aluminum based alloy, and a titanium based alloy, and wherein the body comprises an outer circumferential surface; advancing a substrate in contact with the outer surface of the nozzle body; removing a portion of the outer surface of the nozzle body with the advancing substrate to define a recessed area; filling the recessed area with one or more abrasion resistant materials, the one or more abrasion resistant materials being different from the first material; and fusing the one or more abrasion resistant materials to the nozzle body in the recessed area.

T. The method according to paragraph S, wherein fusing further comprises applying the abrasion resistant material by laser deposition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for applying fluid to an advancing substrate, the apparatus comprising:
    a nozzle body comprising a first material, wherein the first material is selected from the group consisting of: an iron based alloy, an aluminum based alloy, and a titanium based alloy, and wherein the nozzle body comprises:
        a passageway;
        one or more abrasion resistant materials fused to the nozzle body to form a nozzle contact portion adapted to contact the advancing substrate, the one or more abrasion resistant materials comprising a first layer comprising tungsten carbide or vanadium carbide, and a second layer comprising a nickel-based alloy; and
    a shim plate connected with the nozzle body, the shim plate comprising a plurality of slots in fluid communication with the passageway.

2. The apparatus of claim 1, wherein the nozzle body comprises:
    a first nozzle member; and
    a second nozzle member removably connected with the first nozzle member.

3. The apparatus of claim 2, wherein the shim plate is positioned between the first nozzle member and the second nozzle member.

4. The apparatus of claim 2, wherein the first nozzle member or the second nozzle member is free of abrasion resistant material.

5. The apparatus of claim 2, wherein at least one of the first nozzle member and the second nozzle member comprises a nozzle contact portion.

6. The apparatus of claim 1, wherein the one or more abrasion resistant materials comprise a depth of from about 0.5 mm to about 4 mm.

* * * * *